US009732368B2

(12) United States Patent
Pierquin (10) Patent No.: US 9,732,368 B2
(45) Date of Patent: Aug. 15, 2017

(54) DEVICE FOR EARLY DETECTION OF MICRO-ORGANISMS

(71) Applicant: ADVENCIS, Mutzig (FR)

(72) Inventor: Joseph Pierquin, Molsheim (FR)

(73) Assignee: ADVENCIS, Mutzig (FR)

( * ) Notice: Subject to any disclaimer, the term of this patent is extended or adjusted under 35 U.S.C. 154(b) by 0 days.

(21) Appl. No.: 14/374,178

(22) PCT Filed: Jan. 24, 2013

(86) PCT No.: PCT/EP2013/051387
§ 371 (c)(1),
(2) Date: Jul. 23, 2014

(87) PCT Pub. No.: WO2013/110734
PCT Pub. Date: Aug. 1, 2013

(65) Prior Publication Data
US 2015/0031119 A1    Jan. 29, 2015

(30) Foreign Application Priority Data

Jan. 27, 2012  (FR) .................................. 12 50788

(51) Int. Cl.
*C12M 1/34*   (2006.01)
*C12Q 1/04*   (2006.01)
*C12M 1/00*   (2006.01)

(52) U.S. Cl.
CPC .............. *C12Q 1/04* (2013.01); *C12M 41/14* (2013.01); *C12M 41/36* (2013.01)

(58) Field of Classification Search
CPC .......... C12Q 1/04; C12M 41/14; C12M 41/36
See application file for complete search history.

(56) References Cited

U.S. PATENT DOCUMENTS 3,922,905 A * 12/1975 Roth .................... G01N 1/2208
                                                        73/28.04
6,002,789 A    12/1999 Olsztyn
(Continued)

FOREIGN PATENT DOCUMENTS

JP    2005172680 A    6/2005
WO    03022999 A2    3/2003

OTHER PUBLICATIONS

K. Hirota, T. Ono, "Rapid detector of microorganisms, useful for detecting target microorganisms, comprises substrate immobilized with substance for trapping target microorganisms, and apparatus for optically detecting target microorganisms," Database WPI Week 200621 Thomson Scientific, London, GB; vol. 2006, Nr:21, AN 2006-197819 XP002684558, Abstract Only.

*Primary Examiner* — William H Beisner
(74) *Attorney, Agent, or Firm* — Andrew W. Chu; Craft Chu PLLC (57) ABSTRACT

The device permitting an early detection, without measurement of the fluorescence, of colonies resulting from the multiplication of micro-organisms present in a sample to be tested, includes a substantially flat and horizontal detection surface, on which at least one support for growing the micro-organisms in the form of colonies is arranged immobile. The support is of the type membrane or agar medium. There is a detection system, such as a linear scanner, mounted movable and flat for scanning the whole or part of the surface, including at least one CCD sensor associated with an optical system comprised of at least one lighting and at least one optical device, such as a lens. The CCD sensor has a resolution higher than or equal to 2400 dpi. The detection system images colonies having a diameter smaller than 50 [mu]m through a useful magnification higher than or equal to 60.

11 Claims, 3 Drawing Sheets

(56) References Cited

U.S. PATENT DOCUMENTS

| | | | |
|---|---|---|---|
| 6,271,022 B1 * | 8/2001 | Bochner | G01N 35/028 356/388 |
| 6,750,006 B2 * | 6/2004 | Powers | C12Q 1/04 435/4 |
| 2002/0058862 A1 * | 5/2002 | Furnas | G02B 21/365 600/300 |
| 2003/0155528 A1 | 8/2003 | Tokuda | |

* cited by examiner

DEVICE FOR EARLY DETECTION OF MICRO-ORGANISMS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is related to the field of the detection of micro-organisms in the growth phase.

The present invention will find its application mainly in the field of industrial microbiology, for example in the pharmaceutical, biotechnological or agro-food industries.

The invention relates in particular to a device permitting an early detection of the forming of colonies, based on micro-organisms present in the sample, at the surface of a membrane or a solid or semi-solid growth medium.

2. Description of Related Art Including Information Disclosed Under 37 CFR 1.97 and 37 CFR 1.98

Many techniques are presently implemented to permit the detection of contaminants, for example bacteria, in a sample to be tested.

The most common and oldest method consists of a deposition at the surface of an agar growth medium, where the latter can be more or less selective for one or several types of microorganisms. The medium is then incubated at the proper temperature for the growth of the micro-organism looked for, during a time period that may often extend up to several days.

Such a method has the drawback of requiring a relatively long incubation period in order to permit detection visible to the naked eye of the colonies that formed on the agar.

Also known from the state of the art is to perform a chain polymerization reaction, also referred to as PCR amplification, in order to determine the presence of specific micro-organisms within a sample, through amplification of a DNA or RNA sequence.

These methods have the drawback of requiring several DNA strands, i.e. several contaminating micro-organisms, generally at least several dozens of micro-organisms. Such methods are thus less sensitive than the methods based on the growth.

Also known is the possibility of using techniques consisting in marking the micro-organisms so as to emphasize the contrast between the light emitted by the micro-organisms and that emitted by the growth support. The use of specific fluorescent markers, the fluorophores, or of enzymes permitting to reveal the bioluminescence emitted for example by the [Alpha][Tau][Rho] (adenosine triphosphate), permits to detect the micro-organisms early, thanks to the use of optical systems sensitive to the characteristics of the emitted light, for example the wavelength or the intensity.

Known is thus namely the American patent application US 2003/0155528, which describes a method for detecting microorganisms, in which the latter are marked by means of appropriate fluorescent reagents permitting, on the one hand, in order to determine the quantity of micro-organisms and, on the other hand, to judge whether they are viable or dead cells.

These techniques can however prove heavy to be implemented and require the use of often expensive reagents and the presence of qualified labor. In addition, they are not well-suited for the detection of contaminants on a large number of samples, the marking operation being often difficult to be automated. Finally, these techniques exhibit a risk of contaminating the sample. Indeed, the addition of reagents requires a bringing into contact of said reagent with the micro-organisms to be detected.

In the state of the art are also known methods based on a use of the properties of light emitted naturally by the microorganisms, by detecting for example the self-fluorescence of said micro-organisms. Thus, it is possible to facilitate the distinction of colonies by using the contrast existing between the natural fluorescence emitted by said micro-organisms and the non-fluorescent support on which they have been arranged.

A method using this principle is described namely in international patent application WO 03/022999, in which determined optical properties of the colonies are used, such as the self-fluorescence.

These techniques permit indeed to facilitate the detection of colonies or of the self-fluorescent micro-organisms, the latter then presenting a better contrast with the membrane or the growth medium. However, the level of fluorescence generated naturally is of low amplitude, which does not permit to obtain fast detection times, compared for example with a marking with a specific fluorophore. In addition, the parasitic emission of natural fluorescence by the growth medium or by other particles present in the environment, such as dust, fibers of membranes or plastic particles proceeding from the support, can generate a falsely positive result.

Finally, techniques using systems with high optical magnification can be used to view colonies at early stages of development: this is the case for example for microscopes. Nevertheless, these devices are limited to detection on small surfaces, generally smaller than 1 mm$^2$. Thus, the implementation of this type of techniques for the detection on one or several detection supports, such as membranes or agar media, proves both long, in the range of several minutes per cm$^2$, and expensive, because of the necessity of using scanning systems.

SUMMARY OF THE INVENTION

The invention provides the possibility of coping with the various drawbacks of the state or the art by providing a device permitting an early detection, and which can be automated, of the apparition of colonies at the surface of a growth support, namely a membrane or an agar growth medium.

Moreover, the device according to the present invention permits to omit the use of expensive equipment or reagents requiring the presence of a qualified operator.

To this end, the present invention relates to a device permitting a rapid detection, without measurement of the fluorescence, of colonies resulting from the multiplication of micro-organisms present in a sample to be tested, said device comprising:

a substantially flat and horizontal detection surface, on which at least one support for growing the microorganisms in the form of colonies is arranged immobile, this support being of the type membrane or agar medium, a detection system, such as a linear scanner, mounted movable and flat for scanning the whole or part of said surface, including at least one CCD or CMOS sensor, which an optical system comprised of at least one lighting and at least one optical means, such as a lens, is associated with.

The CCD or CMOS sensor of the detection system has a resolution higher than or equal to 2400 dpi, and said detection system permits the detection by imaging of colonies having a diameter smaller than 50 μm through a useful magnification higher than or equal to 60.

Yet more preferably, the CCD sensor of the detection system has a resolution higher than or equal to 4800 dpi.

Preferably, said surface has an A5 or A5*2<n> format, n being an integer higher than or equal to 1.

According to a particularly advantageous embodiment, the optical system has a field depth higher than or equal to 4 mm.

In an interesting way, the detection system is located above said surface.

Preferably, said surface consists of a drawer capable of passing from an open position, for receiving the growth supports, to a closed position, in which it permits a scanning of said supports by said detection system, said supports being arranged directly in said drawer or on at least one tray aimed at being placed in said drawer.

Yet more preferably, the tray includes a plurality of recesses capable of receiving the growth supports.

Advantageously, the optical system of the movable detection system includes a mirror, a light emitting diode lighting and a lens.

According to another peculiarity of the invention, the present device also includes a heating system for maintaining the growth support or supports arranged on said detection surface at a substantially constant temperature. The latter advantageously permits to maintain the growth support or supports at a temperature between 22[deg.] C. and 55[deg.] C.

In an interesting way, the movable detection system includes an imaging system permitting to take images and an analysis of high-resolution images at regular time intervals, said images having a size larger than or equal to 100 million pixels.

The present invention includes many advantages. On the one hand, the large size of the detection surface permits the simultaneous analysis of several growth supports, namely such as membranes or agar media. Indeed, the number of samples analyzed simultaneously by the device according to the invention can be as high as several dozen. Thus, thanks to the device according to the invention, it is possible, in a small period of time, to obtain a larger number of results, compared to the presently existing detection techniques.

In addition, according to the present device, the growth supports being analyzed can preferably be immobile on the detection surface and, hence, must not be moved; the detection system is movable. In contrast, in the existing systems the samples to be analyzed are generally piled up and are brought individually to the detector, for example the microscope or the camera, either manually or namely through a robotized arm. However, the manipulation of the sample, whether manually or automatically, is critical for a rapid detection system: it can indeed be a cause for contamination by micro-organisms or by other small-size parasitic particles, such as dust, which can result into a false detection of colonies, also of a small size.

It is also possible to include into the device according to the invention means permitting the incubation of the growth supports, in particular heating means permitting to maintain the supports at a substantially constant temperature. Thus, said supports can be analyzed during their incubation, which permits to avoid the growth supports from being moved from the incubator to the detection system and thus to reduce the detection time.

On the other hand, the use of a high-resolution detection system including namely at least one linear CCD sensor and an optical means with a large field depth permits to detect colonies of a very small size and completely invisible to the naked eye, in the range of a few dozens of micrometers. Thus, the detection of contaminants in a sample occurs early. Moreover, the scanning time for the different samples is relatively short, in the range of a few seconds per cm<2>, compared to the time necessary for performing a scanning of one or several samples by means of a microscope, for which it is recalled that the scanning time is estimated at several minutes per cm<2>.

BRIEF DESCRIPTION OF THE DRAWINGS

Further features and advantages of the invention will become clear from the following detailed description of the non-restrictive embodiments of the invention, with reference to the attached figures.

FIG. 3 is a schematic illustration of the detection system of the device according to the invention. In particular.

FIG. 6 corresponds to graph illustrations of three images taken successively, at t1=12 h (FIG. 6A), t2=24 h (FIG. 6B) and t3=36 h (FIG. 6C), of growth supports seeded with bacteria of the Mefcylojacfceriujn species, the applied magnification being of 150.

DETAILED DESCRIPTION OF THE DRAWINGS

The device 1 according to the present invention permits a particularly early detection of contaminating micro-organisms, such as bacteria, yeasts, mycoplasmas, moulds, eventually present in a sample that must be analyzed. Indeed, such a device permits to detect colonies even when they are still invisible to the naked eye and, in addition, using the light emitted naturally by said colonies, without addition of a reagent and without measurement of the natural or self fluorescence. Such a device is namely represented in the attached FIGS. 2 and 3.

As regards the samples that must be analyzed, they can namely proceed from industries working in various fields, such as the pharmaceutical, agro-food, biotechnological or even cosmetic industries. Indeed, in this kind of industries, it is particularly interesting, and even necessary, to quickly detect the presence of eventual contaminants. Indeed, the products manufactured and/or transformed in this kind of industry are particularly sensitive, namely because of their destination (food, consumers' health, etc.) and it is essential to ensure as quickly as possible that their microbiological quality is irreproachable.

Thus, in a first step, the samples proceeding from these industries must be prepared in order to be arranged thereafter in the detection device 1 according to the present invention, to finally be analyzed. The preparation of the samples is shown in the attached FIG. 1.

Figure 1:
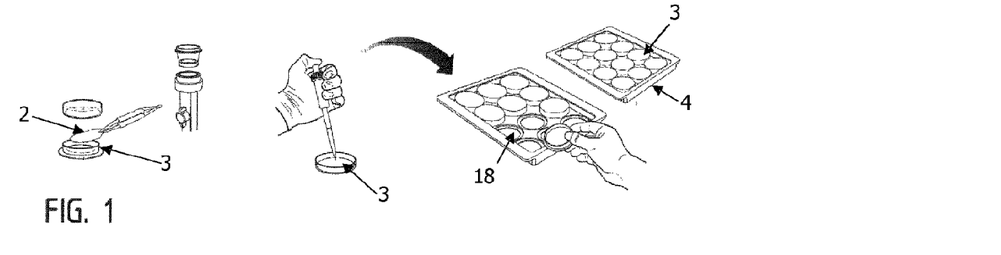
FIG. 1 is a schematic view of a representation of the preparation of the samples that must be analyzed.

When the sample consists of any liquid medium whatsoever, for example a beverage, a medicine to be taken as a beverage or a liquid cosmetic lotion, it can be filtered through an adapted filtering membrane 2. Then, said membrane 2 can advantageously be placed on the surface of a support 3 capable of permitting a bacterial growth, for example a nutrient agar.

According to another embodiment, namely when the volume to be analyzed is small, it is possible to proceed to a direct taking from the liquid sample, then to place it on the surface of a growth support 3.

The growth supports 3, which can be such as a membrane or agar medium, thus permit the growth and the multiplication of the isolated micro-organisms eventually present in the sample to be analyzed. The multiplication of these micro-organisms will result into the forming of colonies at the surface of said supports 3.

The thus seeded growth supports 3 can then be loaded onto a tray 4, as shown in FIG. 1, said tray 4 being capable of receiving at least one, and preferably a plurality of, growth supports 3. Indeed, the tray 4 can preferably include at least one recess 18 provided for in the thickness of the tray 4, said recess 18 being capable of receiving a growth support 3.

The tray 4 can then be loaded into the device 1 according to the invention, so as to permit the detection of colonies forming on the surface of said supports 3.

The use of a tray 4 is advantageous because it permits to facilitate the displacement of a plurality of supports 3 at the same time. In addition, said tray 4 is autoclavable, which permits to promote its cleaning.

However, such an embodiment should not be considered as restricting the invention, since the growth supports 3 can also be placed directly, without previous positioning on the tray 4, on a substantially flat surface of the detection device 1 according to the present invention.

Figure 2:
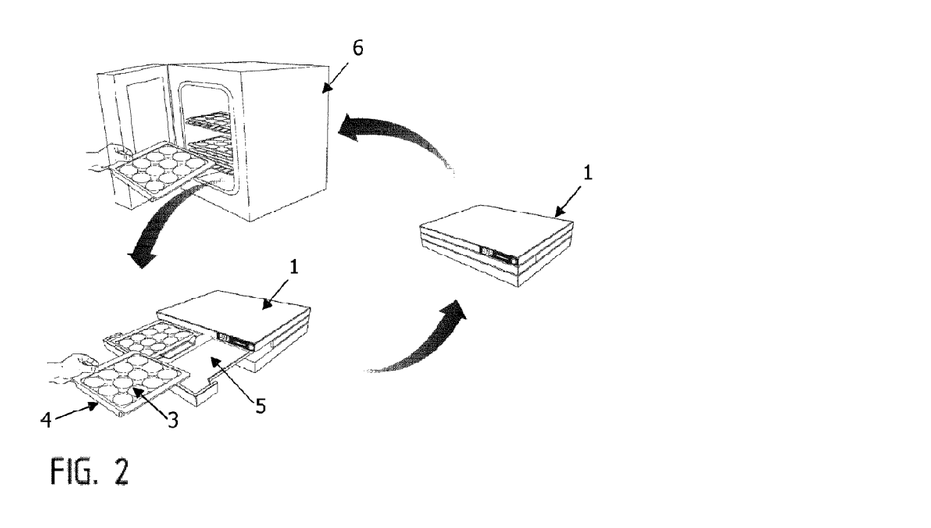
FIG. 2 is a schematic view, showing an embodiment of the invention, in which the device does not incorporate directly a means permitting the incubation of the growth media.

Turning back now to said device 1, it is represented, in one of its embodiments, in the attached FIG. 2.

The detection device 1 according to the invention includes, on the one hand, a preferably substantially flat and horizontal detection surface 5, on which at least one seeded growth support 3 can be arranged according to the above indications. Preferably, a plurality of growth supports 3 are placed on said surface 5, so as to permit a simultaneous detection of eventual contaminants present in several samples.

Thus, the size of the detection surface 5 should be adapted in order to permit to receive a plurality of supports 3, for example 24 supports 3, whereby the latter can preferably be placed on said surface 5 through at least one tray 4. Therefore, the surface 5 has preferably a minimum surface area corresponding substantially to an A5 format, i.e. at least 31000 mm$^2$. Yet more preferably, said detection surface 5 has an [Alpha]4 or even A3 type format.

In summary, the detection surface 5 has advantageously an A5 format or an A5*2$^{<n>}$ format, n being an integer larger than or equal to 1. Thus, said detection surface 5 permits to receive a large number of growth supports 3, so as to simultaneously process several samples.

The device 1 according to the present invention includes on the other hand a detection system 7, for example such as a scanner, mounted movable and permitting to scan at least part, and preferably the whole, of the detection surface 5. Such a detection system is represented in the attached FIG. 3.

Thus, the growth support or supports 3 remain immobile on the surface 5, while the detection system 7 is movable to permit the detection. This permits to avoid a movement of the supports that can be a cause for errors in the results obtained.

Generally, a detection system 7 comprises a light beam scanning the surface 5 on which for example at least one growth support 3 is arranged. A sensor permits to transform the light received into an electric signal, which can then be saved or analyzed.

The detection system 7 of the device 1 according to the present invention preferably includes at least one CCD sensor 8 (Charge-Coupled Device) or one CMOS-type sensor (Complementary Metal Oxide Semi-Conductor).

The CCD sensor 8 of the device 1 according to the invention is generally associated with an optical system, which is in turn comprised of at least one lighting 9, at least one mirror 11 and at least one optical means, for example such as a lens 10.

According to a particularly preferred embodiment, the CCD sensor 8 of the detection system 7 of the detection device 1 according to the invention has a resolution higher than or equal to 4800 dpi (dot per inch), so as to permit the detection by imaging of the colonies present on the growth supports 3 when these have a diameter smaller than or equal to 50 urn, even smaller than 20 um, through a useful magnification larger than or equal to 60.

Indeed, the resolution of the CCD sensor 8, when it is higher than or equal to 4800 dpi, i.e. about 5 microns, permits to achieve a useful magnification, which corresponds to the ratio between the actual size of the colony and its image restituted without interpolation to the user, larger than or equal to 60.

Thus, the device 1 according to the invention permits to restitute an image corresponding to at least 60 times the actual size of the colony and this without loss of quality at the level of the image. Thus, thanks to this level of optical resolution, it is not necessary to use pixel interpolation techniques, and the magnification is obtained without loss of information. Through the use of at least one CCD sensor 8 having such a resolution, the detection of the forming of colonies at the surface of a support 3, starting from isolated micro-organisms in a sample, is extremely early.

Such a resolution higher than or equal to 4800 dpi for the CCD sensor 8 is ideal; however, good results are also obtained with a CCD sensor 8 having a resolution higher than or equal to 2400 dpi, i.e. about 10 microns.

The magnification achieved by the detection system 7 can also be achieved, at least partially, through the lens 10.

Thus, the detection system 7 of the device 1 permits to display a colony when the latter has a diameter in the range of a few micrometers, for example 20 [mu][pi][iota], while the naked eye does not perceive anything below about one hundred micrometers at a usual distance for reading a sample, this distance being typically in the range of 30 centimeters. The present device 1 thus permits a rapid detection of the presence of eventual contaminants in a sample.

Therefore, a contaminant that would be detected in 5 days using known detection techniques will be displayed, with the device 1 according to the invention, in a maximum of 48 h, and preferably in 24 h or less. Furthermore, such a resolution of the CCD sensor 8 permits very advantageously to detect micro-colonies having a very low contrast with the growth support. Thus, even translucent colonies resulting for example from the multiplication of the germs in water can be detected at a resolution preferably higher or equal to 4800 dpi.

In other words, the resolution of the CCD sensor 8 of the device according to the invention represents a threshold value permitting to detect of a large majority of the micro-colonies, without using techniques aimed at increasing the contrast between the micro-colonies and their growth support, this irrespective of their optical properties and their morphology.

In addition, the use of a detection system 7 including at least one CCD sensor 8 permits to relatively quickly scan several dozens of seeded growth supports 3 from samples to be tested, which is not the case with the traditional industrial systems. Indeed, some dozens of minutes should typically be taken into consideration to analyze some twenty supports 3 arranged on the detection surface 5; on the other hand, the use of a microscope and a scanning system instead of the detection system 7 would require several hours for the analysis.

Figure 3A:
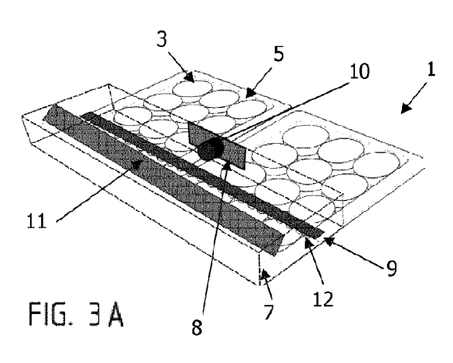
FIG. 3A represents a top plan view, while FIG. 3B corresponds to a cross-sectional view of the device according to the invention.
Figure 3B:
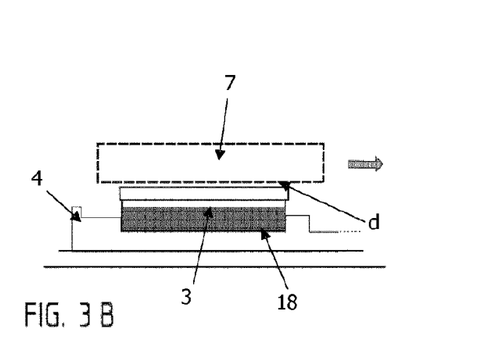

Thus, preferably, as shown namely in FIG. 3B, a growth support 3 is maintained immobile in a recess 18 of the tray 4 during transport and analysis. This advantageously permits a constant positioning of said support 3 with respect to the detection system 7, which will permit the detection of colonies. It is namely necessary to ensure a smallest possible distance between the growth support 3 and the movable detection system 7, typically in the range of 0.5 mm. This minimum distance d is also shown in FIG. 3B.

Therefore, the height of the recess 18 depends on the kind of growth supports 3 used and the use of adapted trays 4 permits the use of different sizes of growth support 3, the height and the diameter of which can vary, for example depending on the sample to be analyzed. Turning back now to the optical system of the device 1 according to the invention, it has, according to a particularly interesting feature, a field depth larger than or equal to 4 mm. The field depth is defined as the area of space in which should be the micro-organism, or the colony, with respect to the movable detection system 7 to be able to obtain a clear image.

Such a field depth, achieved through the use of an adapted optical means, for example such as a lens, permits the detection of colonies on the growth support 3, since the agar or the membrane of said support 3, on which the colonies to be detected are found, is located at some distance with respect to the detection system 7. In addition, the surface, on which the micro-organisms grow, is generally not perfectly flat.

Finally, the use of an optical system with a large field depth permits to avoid to constantly proceed to the focusing of high magnification optics; this permits therefore an increase of the scanning speed, which can then be much higher than that of the existing devices.

According to a preferred embodiment of the device 1 according to the invention, which is the one represented in the attached figures, the detection system 7 scanning the detection surface 5 is located above said surface 5. However, such an embodiment does not restrict the invention, and said detection system 7 of the device 1 could also scan the surface 5 from below.

Preferably, the optical system of the movable detection system 7 includes a mirror 11, a lighting 9 with light-emitting diodes 12 and a lens 10. The lighting 9 permits to illuminate the growth supports 3 and the light they reflect is returned by said mirror 11 to the lens 10, which in turn permits to return the reflected light to the CCD sensor 8.

As represented in FIG. 2, the device 1 according to the invention can be used in parallel with a system permitting the separated incubation of the growth supports 3, whereby such a system can namely be an oven 6, and maintaining said supports 3 at a substantially constant temperature, in order to promote the growth of the micro-organisms. The growth supports 3 are then transferred either manually or automatically from the oven 6, in which they are maintained at a particular temperature, to the device 1 according to the invention, in which the detection of a colony will be performed. The growth supports 3 are preferably arranged on a tray 4, which permits to facilitate their displacement from the oven 6 to the detection device 1.

However, it is even more advantageous for the detection device 1 according to the invention to directly incorporate a heating system capable of maintaining the growth supports 3 at a substantially constant temperature at the level of the detection surface 5. Such a particular embodiment is represented in the attached FIG. 4.

Figure 4:
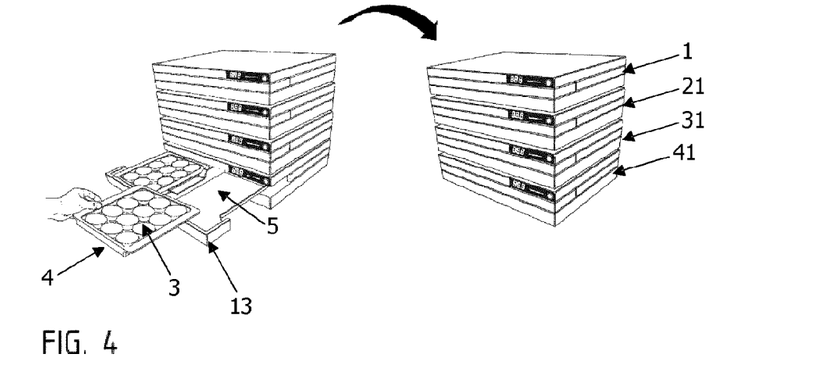
FIG. 4 represents a schematic view of a different embodiment, in which the device incorporates directly a system for maintaining at a constant temperature which permits the incubation of the growth supports.

Thus, the detection surface 5 can preferably consist of a drawing 13 including at least one substantially flat surface permitting to load the growth supports 3, either directly or through at least one tray 4, onto said surface of the drawer 13. The latter is advantageously closed laterally, thus facilitating the maintaining of said supports 3 at a substantially constant temperature, through adapted means, for example a heating system. However, putting into place a drawer 13 can also be useful when the growth supports 3 are passed from an oven 6 to the device 1.

Preferably, the drawer 13 permits to receive two trays 4 on which the growth supports 3 are arranged, advantageously in recesses 18, as can be seen namely in the attached FIG. 4. Each of the growth supports 3 is thus preferably positioned in an adapted recess 18.

The tray 4 then advantageously permits to maintain a constant and minimum distance between the growth supports 3 and the CCD sensor 8 of the detection system 8.

The growth supports 3 are advantageously maintained at a temperature between 22[deg.] C. and 55[deg.] C., depending for example on the optimum temperature for the growth of a particular micro-organism one wants to detect preferably in a sample. The advantage resulting from maintaining the growth supports 3 at a constant temperature consists in permitting a reduction of the number of operations to be performed in order to achieve a result. This also facilitates the automation of the detection by the device 1 according to the invention, which permits, as a result, a reduction of the time for detecting colonies.

According to a particular embodiment, also represented in the attached FIG. 3, a plurality of detection devices 1, 21, 31 and 41 according to the invention can also be piled up above each other, in order to permit place saving and a detection of eventual contaminants in a larger number of starting samples.

Such an embodiment is possible, on the one hand, because of the relatively low cost of a detection device 1 and, on the other hand, because of the limited height of said device 1, usually in the range of some ten centimeters. This particular embodiment could not be implemented for example if a detection system based on a standard camera were used, this type of system being privileged in the presently existing devices.

The device 1 according to the invention can also incorporate an imaging system permitting on the one hand a taking of successive images of the growth supports 3, at a regular time interval, and on the other hand the analysis of said images in order to detect micro-colonies.

Such an imaging system should be capable of managing particularly large image sizes, due to the high resolution, higher than or equal to 4800 dpi, of the CCD sensor 8 of the detection system.

Indeed, with such a resolution level, the size of the images obtained is in the range of 100 million pixels; within an image of this size, a micro-colony represents about twenty pixels. In other words, the ratio between the size of the image to be analyzed and that of the element to be detected, i.e. the micro-colony, is generally higher than 1 million, which requires an adapted imaging system. Indeed, in the field of the imaging, a detection based on images of a size in the range of 100 million pixels, and the taking into consideration of a size ratio higher than 1 million are generally not possible with traditional image-processing software available on the market.

The imaging system preferably includes image-analyzing means permitting a comparison of the images taken at regular intervals, so as to highlight an apparition and/or a growth of the colonies on the growth support or supports 3 arranged on the detection surface 5.

Figure 5:
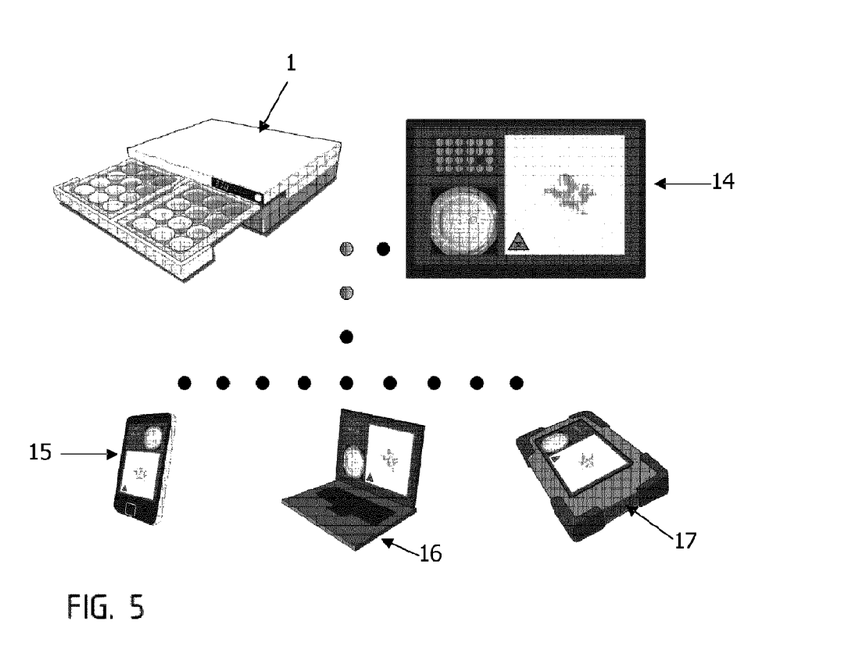
FIG. 5 represents a schematic view of the analysis of the results by the device according to the invention, and the transmission of the information of the device on a screen or another peripheral device.

Advantageously, said system also comprises at least one screen 14 permitting to display the images of the growth supports 3 that have been taken, as shown in FIG. 5.

The images can also be transmitted by any adapted means to peripheral devices consisting namely of Smartphones 15, portable computers 16 or also tablets 17.

Yet more preferably, such means permitting a comparison of images are capable of permitting the detection of the colonies by comparison of images, said comparison being performed between an image taken at time t and an image previously taken at time t−1.

The operation of comparing successive images advantageously permits the operator to distinguish a growing colony from a contamination (dust, etc.) of the growth support 3, since the size of the contamination does not vary between two takings of images. Therefore, the taking of a decision regarding the presence or not of micro-organisms in a starting sample is facilitated.

Figure 6A:
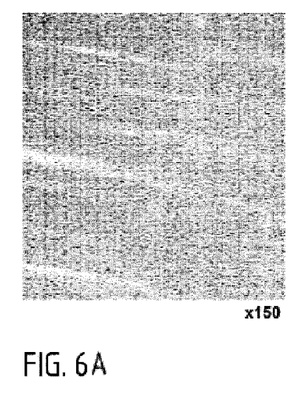
Figure 6B:
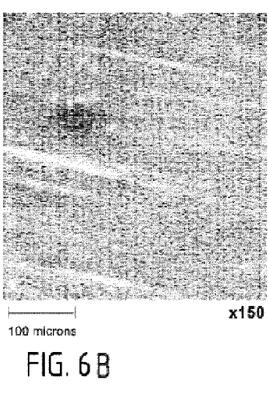
Figure 6C:
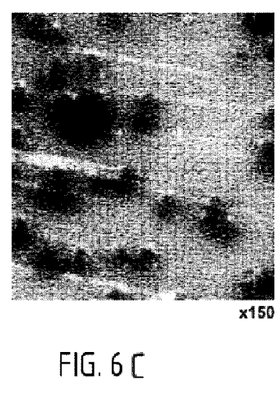

An exemplary result obtained during the detection by taking of successive images with the device 1 according to the present invention is shown in the attached FIGS. 6A, 6B and 6C. The magnification applied here is 150. One can see, when comparing the two images taken successively at t=12 h and t=24 h, corresponding respectively to FIGS. 6A and 6B, after seeding the growth support with micro-organisms of the Methylobacterium species, that a micro-colony has appeared. The image taken at 24 h, shown in FIG. 6B permits to conclude with certainty of the presence of a contamination. The image taken at t=36 h, shown in FIG. 6C, permits to display all the colonies present on the surface considered, though their size does not yet permit them to be visible to the naked eye, this size being smaller than 100 urn. The detection by the naked eye becomes sure not sooner than 48 h after seeding, and all the colonies on the whole of the detection support, here a membrane, can be counted in a sure way after 4 days in this example. The device 1 thus permits an extremely early detection of micro-organisms in a starting sample.

The present invention has also further advantages: on the one hand, the detection system used in the device 1 is very cheap, namely compared to the existing systems in the state of the art, and using expensive equipment or reagents. On the other hand, the possible automation of the device also promotes the reduction in time of the detection of the contaminants.

Of course, the invention is not restricted to the examples shown and described above, which can have variants and modifications without departing from the scope of the invention.

I claim:

1. A device for early detection of colonies resulting from multiplication of micro-organisms, said device comprising:
    a substantially flat and horizontal detection surface;
    at least one support fixedly attached to the detection surface, said at least one support growing micro-organisms as colonies, the support being selected from a group consisting of a type membrane and agar medium; and
    a detection means, being moveably mounted and aligned flat with the detection surface, said detection means being comprised of at least one sensor, and an optical system associated with said at least one sensor, said optical system being comprised of at least one lighting source and at least one optical means,
    wherein the sensor has a resolution higher than or equal to 2400 dpi, and
    wherein said optical means magnifies higher than or equal to 60.

2. The device for early detection, according to claim 1, wherein the sensor has a resolution higher than or equal to 4800 dpi.

3. The device for early detection, according to claim 1, wherein the detection surface has a format selected from a group consisting of an A5 and A5*2<n> format, n being an integral higher than or equal to 1.

4. The device for early detection, according to claim 1, said optical system has a field depth higher than or equal to 4 mm.

5. The device for early detection, according to claim 1, wherein said detection means is located above the detection surface.

6. The device for early detection, according to claim 1, wherein the detection surface is a drawer, being comprised of a drawer portion (13) said drawer having an open position, said at least one support being placed on the detection surface in said open position, and a closed position, said at least one support being aligned with detection means in said closed position, said device further comprising:
    a tray removable engaged on the detection surface as said drawer, said at least one support being fixedly attached to said tray,
    wherein said at least one support being arranged in at least one of a group consisting of: directly in said drawer, and on said tray with said tray being placed in said drawer.

7. The device for early detection, according to claim 6, wherein the tray is comprised of a plurality of recesses, each recess corresponding to a respective at least one support.

8. The device for early detection, according to claim 1, wherein said optical system comprises a mirror, a lighting source with light-emitting diode, and a lens.

9. The device for early detection, according to claim 1, further comprising:
   a heater arranged on the detection surface, said heater setting a substantially constant temperature.

10. The device for early detection, according to claim 9, wherein said substantially constant temperature is selected from a temperature between 22 [deg.] C. and 55 [deg.] C.

11. The device for early detection, according to claim 1, further comprising:
   a display means in communication with the detection means, said detection means being mobile, said display means being mobile and being a screen selected from a group consisting of: a smartphone screen, a portable computer screen, and a tablet computer screen, said screen displaying images having a size larger than or equal to 100 million pixels.

* * * * *